United States Patent [19]

Okada et al.

[11] Patent Number: 5,087,705

[45] Date of Patent: Feb. 11, 1992

[54] PROCESS FOR PREPARATION OF N-SUBSTITUTED MALEIMIDES

[75] Inventors: Takashi Okada; Takamichi Aoyama; Shoichi Mizuno; Akihiro Akatsuka, all of Yokkaichi; Kiyonari Matsuoka, Mie, all of Japan

[73] Assignee: Shin-Daikyowa Petrochemical Co., Ltd., Tokyo, Japan

[21] Appl. No.: 510,884

[22] Filed: Apr. 18, 1990

[30] Foreign Application Priority Data

Apr. 21, 1989 [JP] Japan ................................. 1-102891
Sep. 7, 1989 [JP] Japan ................................. 1-232142
Sep. 7, 1989 [JP] Japan ................................. 1-232143

[51] Int. Cl.$^5$ ............................................ C07D 207/444
[52] U.S. Cl. ............................................ 548/458
[58] Field of Search ............................................ 548/548

[56] References Cited

U.S. PATENT DOCUMENTS 2,444,536  7/1948  Searle ................................. 260/313
4,171,302  10/1979  Abblard et al. ................ 260/239 A

FOREIGN PATENT DOCUMENTS 165574  12/1985  European Pat. Off. .
0213933  3/1987  European Pat. Off. .
5140078  11/1976  Japan .
5368770  6/1978  Japan .
62215563  9/1987  Japan .

OTHER PUBLICATIONS

*Chemische Berichte*, Helferich et al., vol. 100, 1967, pp. 421-424.
Tsutomu Oishi et al., "Syntheses and Thermostabilities of N-Substituted Maleimide Copolymers. III. N-Isopropylmaleimide, N-sec-Butylmaleimide and N-tert-Butylmaleimide".
*Technology Reports of the Yamaguchi University*, vol. 4, No. 2, Dec. 1988, 152-159.

*Primary Examiner*—David B. Springer
*Attorney, Agent, or Firm*—Wegner, Cantor, Mueller & Player

[57] ABSTRACT

N-substituted maleimide represented by formula (2):

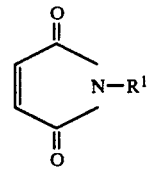

is produced from N-substituted maleamic acid monoester represented by formula (1):

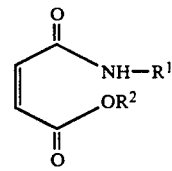

in the presence of an acid catalyst by elmination of an alcohol from the monoester. The above N-substituted maleamic acid monoester represented by formula (1) is produced by esterification of N-substituted maleamic acid represented by formula (3):

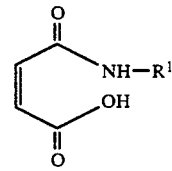

with an alcohol $R^2$-OH in the represence of an acid catalyst.

19 Claims, 2 Drawing Sheets

FIG. 2

PROCESS FOR PREPARATION OF N-SUBSTITUTED MALEIMIDES

BACKGROUND OF THE INVENTION

1. Field of the Invention

The present invention relates to a process for preparation of N-substituted maleimides. The N-substituted maleimides are useful compounds as agent for modifying heat resistance of resins such as ABS, MMA and PVC, and as intermediate of pharmaceuticals and pesticides.

2. Description of Prior Art

Various processes for preparation of maleimides have been studied. Among them, the most general process is one described in U.S. Pat. No. 2,444,536 in which a maleimide is produced by dehydration of a maleamic acid with a dehydration agent such as acetic anhydride. In detail, maleic anhydride is reacted with an amine compound and the resulting maleamic acid is dehydrated in the presence of acetic anhydride and sodium acetate to perform an imidation reaction and obtain the maleimide.

However, this process requires one or more equivalents of expensive acetic anhydride based on the maleamic acid in the imidation reation. Further, since a large amount of water is used for separation and recovery of the maleimide produced in the reaction, a large quantity of waste water containing acetic acid is produced and a considerable cost is necessitated to treat this waste water. For these reasons, this process is not suitable to utilize in industrial production.

Japanese Patent Disclosure (Kokai) No.53-68770 discloses a process in which maleic anhydride is reacted with an amine compound in an organic solvent, and the resulting maleamic acid is dehydrated in the presence of a nonproton polar solvent and an acid catalyst without further separation from a reaction mixture to obtain a maleimide. This process, however, has the following disadvantages. Since a large amount of the expensive and toxic nonproton polar solvent such as dimethylformamide has to be used, a cost for preparation of the maleimide is relatively high. The nonproton polar solvent is deteriorated by the action of acid catalyst and losses of the nonproton polar solvent are significant. Since the boiling point of the nonproton polar solvent such as dimethylformamide is relatively high, removal of the solvent from the final product containing the maleimide is quite difficult.

Japanese Patent Publication (Kokoku) No.51-40078 discloses the process in which solvents having 80° C. or more of boiling point are used and an N-substituted maleamic acid is dehydrated by heating in the presence of an acid catalyst such as chlorosulfonic acid and removing water generated in the dehydration together with the solvent by azeotropy to obtain a maleimide. This process is excellent because a large amount of expensive dehydration agent such as acetic anhydride is not required, and separation and recovery of the maleimide are easy.

All of the above-mentioned precesses are directed to a processes for preparation of N-substituted maleimides by dehydration of maleamic acids.

Aside from these processes, Japanese patent Disclosure (Kokai) No.62-215563 discloses the process in which a maleic acid monoester is reacted with an isocyanate compound to obtain a maleamic acid monoester and then this monoester is heated to eliminate an alcohol and obtain an N-substituted maleimide. This process, however, requires high degrees of vacuum in the elimination of alcohol and uses the isocyanate compound which is relatively expensive. For these reasons, this process is not suitable to utilize in industrial production.

Among N-substituted maleimides, cycloalkyl substituted and alkyl substituted ones are noted because these maleimides are colorless and can improve heat resistance of colorless resins such as MMA and PVC without coloring them.

The inventors of this invention tried to apply the process described in Japanese Patent Publication (Kokoku) No. 51-40078 mentioned above to the cycloalkyl substituted maleimides. But the yields of these maleimides are extremely lower than that of the maleimides substituted with an aromatic group.

An object of the present invention is to provide a process for preparation of maleimides including cycloalkyl substituted ones in good yield, irrespective of N-substituents.

Another object of the present invention is to provide a process for preparation of maleimides in high selectivity.

SUMMARY OF THE INVENTION

The present invention relates to a process for preparation of the N-substituted maleimide represented by formula (2):

from the N-substituted maleamic acid monoester represented by formula (1):

wherein $R^1$ represents an unsubstituted or substituted alkyl group having 1 to 20 carbon atoms, an unsubstituted or substituted cycloalkyl group having 3 to 12 carbon atoms, an unsubstituted or substituted phenyl group, or an unsubstituted or substituted naphthyl group; and $R^2$ represents an unsubstituted or substituted alkyl group having 1 to 7 carbon atoms, or an unsubstituted or substituted cycloalkyl group having 3 to 7 carbon atoms, wherein said N-substituted maleamic acid monoester is heated in the presence of an acid catalyst to eliminate an alcohol from the monoester.

Further, the present invention relates to a process for preparation of the N-substituted maleimide wherein the N-substituted maleamic acid monoester represented by formula (1) is produced by esterification of the N-substituted maleamic acid represented by formula (3):

wherein R¹ represents an unsubstituted or substituted alkyl group having 1 to 20 carbon atoms, an unsubstituted or substituted cycloalkyl group having 3 to 12 carbon atoms, an unsubstituted or substituted phenyl group, or an unsubstituted or substituted naphthyl group, in the presence of an acid catalyst and an alcohol represented by R²—OH, wherein R² represents an unsubstituted or substituted alkyl group having 1 to 7 carbon atoms, or an unsubstituted or substituted cycloalkyl group having 3 to 7 carbon atoms.

BRIEF DESCRIPTION OF THE DRAWINGS

The objects and features of the invention may be understood with reference to the following detailed description of the invention, taken together with the accompanying drawings in which.

The present invention will now be explained below.

In formulas (1), (2) and (3), R¹ represents an unsubstituted or substituted alkyl group having 1 to 20 carbon atoms, preferably 3 to 12 carbon atoms, an unsubstituted or substituted cycloalkyl group having 3 to 12 carbon atoms, preferably 5 to 10 carbon atoms, an unsubstituted or substituted phenyl group, or an unsubstituted or substituted naphthyl group. Especially, it is preferred that R¹ represents an unsubstituted or substituted alkyl group having 3 to 12 carbon atoms, or an unsubstituted or substituted cycloalkyl group having 5 to 10 carbon atoms.

The alkyl group includes straight-chain and branched-chain alkyl groups. Preferred examples of the alkyl group include methyl, ethyl, n-propyl, iso-propyl, n-butyl, iso-butyl, sec-butyl, tert-butyl, n-hexyl, n-octyl, n-decyl, n-dodecyl and n-octadecyl.

Preferred examples of the cycloalkyl group include cyclopropyl, cyclobutyl, cyclopentyl, cyclohexyl, cycloheptyl, cyclooctyl and cyclododecyl.

In the present invention, the above alkyl, cycloalkyl, phenyl and naphthyl groups may be unsubstituted or substituted. Examples of substituents include an alkyl group having 1 to 10 carbon atoms, a phenyl group and a halogen atom such as flourine, chlorine and bromine.

The substituted phenyl group is exemplified by methylphenyl, dimethylphenyl, trimethylphenyl, p-ethylphenyl, p-isopropylphenyl, hydroxyphenyl, p-methoxyphenyl, p-ethoxyphenyl, chlorophenyl, bromophenyl and fluorophenyl.

In formula (1) and the alcohol R²—OH, R² represents an unsubstituted or substituted alkyl group having 1 to 7 carbon atoms, preferably 3 to 6 carbon atoms, an unsubstituted or substituted cycloalkyl group having 3 to 7 carbon atoms. Especially, it is preferred that R² represents an unsubstituted or substituted alkyl group having 3 to 6 carbon atoms.

The alkyl group includes straight-chain and branched-chain alkyl groups. Preferred examples of the alkyl group include methyl, ethyl, n-propyl, n-butyl, iso-butyl and n-hexyl.

Preferred examples of the cycloalkyl group include cyclohexyl and cycloheptyl.

In the present invention, the above alkyl and cycloalkyl may be unsubstituted or substituted. Examples of substituents include an alkyl group having 1 to 6 carbon atoms and a phenyl group. The alkyl group having a phenyl substituent is exemplified by a benzyl group.

Examples of the maleamic acid monoester represented by formula (1) are listed below:

methylmaleamic acid methylester, ethylmaleamic acid methylester, n-propylmaleamic acid methylester, iso-propylmaleamic acid methylester, n-butylmaleamic acid methylester, cyclohexylmaleamic acid methylester, n-octadecylmaleamic acid methylester, phenylmaleamic acid methylester, p-nitrophenylmaleamic acid methylester, o-tolylmaleamic acid methylester, p-tolylmaleamic acid methylester, p-chlorophenylmaleamic acid methylester, dichlorophenylmaleamic acid methylester;

methylmaleamic acid ethylester, ethylmaleamic acid ethylester, n-propylmaleamic acid ethylester, iso-propylmaleamic acid ethylester, n-butylmaleamic acid ethylester, cyclohexylmaleamic acid ethylester, n-octadecylmaleamic acid ethylester, phenylmaleamic acid ethylester, p-nitrophenylmaleamic acid ethylester, o-tolylmaleamic acid ethylester, p-tolylmaleamic acid ethylester, p-chlorophenylmaleamic acid ethylester, dichlorophenylmaleamic acid ethylester;

methylmaleamic acid n-propylester, ethylmaleamic acid n-propylester, n-propylmaleamic acid n-propylester, iso-propylmaleamic acid n-propylester, n-butylmaleamic acid n-propylester, cyclohexylmaleamic acid n-propylester, n-octadecylmaleamic acid n-propylester, phenylmaleamic acid n-propylester, p-nitrophenylmaleamic acid n-propylester, o-tolylmaleamic acid n-propylester, p-tolylmaleamic acid n-propylester, p-chlorophenylmaleamic acid n-propylester, dichlorophenylmaleamic acid n-propylester;

methylmaleamic acid iso-butylester, ethylmaleamic acid iso-butylester, n-propylmaleamic acid iso-butylester, iso-propylmaleamic acid iso-butylester, n-butylmaleamic acid iso-butylester, cyclohexylmaleamic acid iso-butylester, n-octadecylmaleamic acid iso-butylester, phenylmaleamic acid iso-butylester, p-nitrophenylmaleamic acid iso-butylester, o-tolylmaleamic acid iso-butylester, p-tolylmaleamic acid iso-butylester, p-chlorophenylmaleamic acid iso-butylester, dichlorophenylmaleamic acid iso-butylester;

methylmaleamic acid n-hexylester, ethylmaleamic acid n-hexylester, n-propylmaleamic acid n-hexylester, iso-propylmaleamic acid n-hexylester, n-butylmaleamic acid n-hexylester, cyclohexylmaleamic acid n-hexylester, n-octadecylmaleamic acid n-hexylester, phenylmaleamic acid n-hexylester, p-nitrophenylmaleamic acid n-hexylester, o-tolylmaleamic acid n-hexylester, p-tolylmaleamic acid n-hexylester, p-chlorophenylmaleamic acid n-hexylester, dichlorophenylmaleamic acid n-hexylester.

Examples of the maleimide represented by formula (2) are listed below:

methylmaleimide, ethylmaleimide, n-propylmaleimide, iso-propylmaleimide, n-butylmaleimide, iso-butylmaleimide, sec-butylmaleimide, tert-butylmaleimide, n-hexylmaleimide, n-octylmaleimide, n-decylmaleimide, n-dodecylmaleimide, n-octadecylmaleimide, cyclohexylmaleimide, 4-methylcyclohexylmaleimide, 2-methyl-cyclohexylmaleimide, allylmaleimide, benzylmaleimide, phenylmaleimide, p-nitrophenylmaleimide, o-tolylmaleimide, p-tolylmaleimide, xylidylmaleimide, p-ethyl-phenylmaleimide, ethoxyphenylmaleimide, p-isopropylphenylmaleimide, p-chloro-phenylmaleimide, dichloro-phenylmaleimide.

Examples of the maleamic acid represented by formula (3) are listed below:

methylmaleamic acid, ethylmaleamic acid, n-propylmaleamic acid, iso-propylmaleamic acid, n-butylmaleamic acid, iso-butylmaleamic acid, sec-butylmaleamic acid, tert-butylmaleamic acid, n-hexylmaleamic acid, cyclohexylmaleamic acid, n-octylmaleamic acid, n-decylmaleamic acid, n-dodecylmaleamic acid, n-octadecylmaleamic acid, 4-methyl-cyclohexylmaleamic acid, 2-methyl-cyclohexylmaleamic acid, allylmaleamic acid, benzylmaleamic acid, phenylmaleamic acid, p-nitrophenylmaleamic acid, o-toylmaleamio acid, p-tolylmaleamic acid, xylidylmaleamic acid, p-ethylphenylmaleamic acid, ethoxyphenylmaleamic acid, p-isopropylphenylmaleamic acid, p-chloro-phenylmaleamic acid, dichloro-phenylmaleamic acid.

The process of the present invention will be explained below:

The maleamic acid monoester represented by formula (1) is heated in the presence of an acid catalyst to eliminate an alcohol from the monoester and form an imide ring (hereinafter, this reaction is called as "imidation"). Examples of the acid catalyst used in this reaction include Brnsted acids. Examples of the Brnsted acids include sulfonic acids such as sulfuric acid, anhydrous sulfuric acid, p-toluene sulfuric acid, methane sulfuric acid, benzene sulfuric acid, ethylsulfonic acid and octylsulfonic acid, and acidic ion exchange resins.

When the amount of the acid catalyst is too small, the progress of the reaction tends to be slow and the reaction time tends to be long. On the other hand, when the amount of the acid catalyst is too high, a large amount of by-products tends to be produced. Therefore, it is suitable to make the amount of acid catalyst from 0.02 to 4 equivalents to the N-substituted maleamic acid monoester represented by formula (1).

It is preferred to conduct the imidation reaction in an organic solvent and any of organic solvents inactive to the maleamic acid monoester, the starting material, and the maleimide, the final product, can be used. Examples of the organic solvent include aliphatic hydrocarbons such as n-hexane, cyclohexane and methylcyclohexane, aromatic hydrocarbons such as benzene, toluene, xylene and isopropylbenzene, and the aromatic hydrocarbons such as benzene and toluene are preferred.

The amount of the solvent may be decided on the basis of the solubility of the maleamic acid monoester. In order to conduct the reaction smoothly and satisfy economical conditions, the weight of solvent suitably ranges from 1 to 20 times, preferably 3 to 15 times of that of the maleamic acid monoester.

It is possible to use two or more of the organic solvents, if necessary.

The imidation reaction can be conducted at a temperature ranging from 80° to 170° C., preferably from 90° to 120° C. for about 1 to 7 hours, preferably 1 to 4 hours. Since this reaction is elimination of alcohol, it proceeds rapidly by removing the generated alcohol by means of azeotropy.

Further this reaction is carried out effectively by previously mixing the maleamic acid monoester with the organic solvent and successively adding this mixture to a refluxing reaction vessel.

In another embodiment of the present invention, an alcohol may positively be caused to coexist with the acid catalyst in the reaction system of the imidation, and it is possible to improve the selectivity of the maleimide represented by formula (2) by the coexistance of the alcohol.

Since the process of the present invention uses the imidation reaction, a lower alcohol concentration should be profitable to production of the maleimide on the basis of the theory of equilibrium. Further a maleamic dialkyl by-product is presumed to be produced by the reaction of the compound represented by formula (1) with the alcohol and therefore, it is considered that the decrease of alcohol concentration is advantageous to the imidation. However, in the process of the invention, results opposite to the above presumption were obtained.

In the process of the present invention, the alcohol is eliminated from the maleamic acid monoester represented by formula (1) in the presence of the acid catalyst together with an alcohol. This alcohol is preferably added to the reaction mixture at the beginning of the reaction. That is, it is preferred that the maleamic acid monoester represented by formula (1) is mixed with the acid catalyst and the alcohol and then the resulting mixture is heated at a reaction temperature.

The alcohol used in this reaction is, for example, an alcohol having an alkyl group having 1 to 7 carbon atoms or a cycloalkyl group having 3 to 7 carbon atoms. Examples of the alcohol include primary alcohols such as methanol, ethanol, n-propanol, n-butanol, iso-butanol, n-hexanol and benzyl alcohol, secondary alcohols such as iso-propanol, sec-butanol and cyclohexanol, tertiary alcohols such as tertbutanol, and diols such as ethyleneglycol. Among them, the primary alcohols are preferred.

The amount of alcohol suitably ranges from 0.1 to 5 equivalents, preferably 0.3 to 3 equivalents to the maleamic acid monoester.

In order to get better selectivity, it is preferred that the acid catalyst, the alcohol and optionally the solvent is prepared previously, followed by heating the resulting mixture, for example, at 50° to 140° C. for 0.1 to 1 hours and then the maleamic acid monoester is added to the mixture.

A method for preparing the maleamic acid monoester will be explained below.

It is preferred that the N-substituted maleamic acid represented by formula (3) is esterified with an alcohol presented by formula $R^2$—OH in the presence of an acid catalyst by removal of the generated water azeotropically to obtain advantageously the N-substituted maleamic acid monoester represented by formula (1).

Better results (high yield of esters) are obtained by using alcohols having an alkyl group with 1 to 7 carbon atoms or a cycloalkyl group with 3 to 7 carbon atoms as the alcohol $R^2$—OH. Examples of the alcohol include primary alcohols such as methanol, ethanol, n-propanol, n-butanol, iso-butanol, n-hexanol and benzyl alcohol, secondary alcohols such as iso-propanol, sec-butanol and cyclohexanol, tertiary alcohols such as tert-butanol, and diols such as ethyleneglycol. Among them, the primary alcohols are preferred.

The amount of alcohol $R^2$—OH suitably ranges from 0.5 to 5 equivalents to the maleamic acid monoester.

Example of the acid catalyst used in this reaction include Brønsted acids. Examples of the Brønsted acids include sulfonic acids such as sulfuric acid, anhydrous sulfuric acid, p-toluene sulfuric acid, methane sulfuric acid, benzene sulfuric acid, ethylsulfonic acid and octylsulfonic acid, and acidic ion exchange resins.

It is suitable that the amount of acid catalyst ranges from 0.01 to 1 equivalents, preferably 0.05 to 0.5 equivalents to the maleamic acid.

It is possible to conduct the esterification in the absence of a solvent but it is preferred to conduct it in the presence of an organic solvent immiscible or insoluble to water. Examples of the organic solvent include aliphatic hydrocarbons such as n-hexane, cyclohexane and methylcyclohexane, and aromatic hydrocarbons such as benzene, toluene and isopropylbenzene. The aromatic hydrocarbons such as benzene and toluene are preferred.

At a higher temperature, the reaction rate increases but at the same time, side reactions occur. Thus the reaction temperature suitably ranges from 30° to 110° C., preferably 50° to 80° C. It is preferred to agitate a reaction mixture. The reaction mixture is continued for about 0.5 to 3 hours while the generated water is taken out from the reaction mixture.

Thus obtained reaction mixtures can be used for the above-mentioned imidation reaction as they are, or after removal of the residual alcohol under a reduced pressure. As a matter of convenience, it is advantageous to use the reaction mixtures as they are.

The imidation reaction can also be conducted by adding a polymerization inhibitor to the mixture containing the maleamic acid monoester represented by formula (1), and heating the mixture at a temperature of from 80° to 170° C., preferably 90° to 120° C. for about 1 to 7 hours, preferably about 1 to 4 hours to eliminate the alcohol. It is provided that the mixture is heated at a temperature higher than that of the esterification mentioned above.

This imidation is carried out in the presence of the same acid catalysts as those used in the above mentioned esterification. The acid catalyst added to the reaction mixture previously at the esterification can be used in the imidation reaction without separation from the product of the esterification. It is provided that an acid catalyst can be supplied freshly at the beginning of the imidation.

Since this imidation is also an alcohol elimination reaction, azeotropical removal of the generated alcohol is advantageous. That is, the alcohol in the reaction mixture is removed azeotropically simultaneously with reflux of a solvent and the solvent removed by the azeotropy is supplied in a reactor successively to keep the amount of solvent constant.

A nonproton polar solvent such as dimethylformamide and dimethylsulfoxide can also be used in the esterification and imidation. Further the polymerization inhibitor can be added to the reaction mixture at the beginning of the esterification.

So far as the reaction temperatures are kept in the above-mentioned range, the reactions can be conducted under an atmospheric, increased or reduced pressure.

Examples of the polymerization inhibitors are listed below:

Alkylmonophenols and alkylbisphenols: phenol, methoxyphenol, tert-butylcatechol, 2,4-dinitrophenol, hydroquinone, tert-butylhydroquinone, 2,6-di-tert-butyl-p-cresol, 2,2'-methylene-bis-(4-methyl-6-tert-butylphenol), 2,2'-methylene-bis-(4-ethyl-6-tert-butylphenol) and 4,4'-thiobis-(4-methyl-6-tert-butylphenol).

Thiodipropionic acid esters: dilauryl thiodipropionate, distearyl thiodipropionate and didodecyl thiodipropionate.

Dithiocarbaminic acid salts: sodium dimethyldithiocarbaminate, sodium diethyldithiocarbaminate, sodium di-n-butyldithiocarbaminate, zinc dimethyldithiocarbaminate, zinc diethyldithiocarbaminate, zinc di-n-butyldithiocarbaminate, nickel dimethyl dithiocarbaminate, nickel diethyldithiocarbaminate and nickel di-n-butyldithiocarbaminate.

Salicyclic acid salts and salicyclic acid ester: sodium salicylate, phenyl salicylate, p-tert-butyl salicylate and p-octylphenyl salicylate.

Phenothiazines: phenothiazine and methylene blue.

Mercaptoimidazoles: 2-mercaptobenzimidazole, zinc salt of 2-mercaptobenzimidazole and 2-mercaptomethylbenzimidazole.

Trialkyl phosphites: triphenylphosphite and diphenylisodecylphosphite.

Copper salts: copper powder, cuprous chloride, cupric chloride, copper sulfate and copper nitrate.

According to the present invention, it is possible to produce alkyl or cycloalkyl substituted maleimides at a relatively lower temperature in good yield and high selectivity. The reaction period necessary to produce the substituted maleimides is shorter than that of the conventional method. Further the color of the product is less than that of the product obtained by the conventional one.

The present invention will be illustrated with reference to examples but the examples are illustrative and not restrictive.

REFERENCE EXAMPLE 1

39.4 g (0.2 mol) of N-cyclohexylmaleamic acid, 180 ml of toluene, 55.3 ml (0.6 mol) of iso-butylalcohol and 2.0 ml of conc. sulfuric acid were added to a four-neck flask (500 ml) equipped with a thermometer, a condenser with a water separator (Dean-Stark trap), a dropping funnel and an agitator. The mixture was heated with stirring under a reduced pressure to keep a reaction temperature at 80° C. and an esterification reaction was conducted for 1 hour by removing water generated by the reaction from the flask. Then the excess amount of iso-butylalcohol was removed from the flask by refluxing and removing 100 ml of the reaction solvent under a reduced pressure.

The resulting reaction mixture was analyzed by high speed liquid chromatography and the composition of the mixture is as follows:

| | |
|---|---|
| N-cyclohexylmaleamic acid iso-butylester | 79.3 mol % |
| N-cyclohexylmaleimide | 16.1 mol % |

EXAMPLE 1

The reaction mixture obtained in Reference example 1 containing N-cyclohexylmaleamic acid iso-butylester was slowly added over a 2 hours-period to 180 ml of toluene which was refluxed with agitation in a four-neck flask (500 ml) equipped with a thermometer, a condenser with a water separator (Dean-Stark trap), a dropping funnel and an agitator. The reaction solvent was removed from the water separator at the same rate as the adding rate of the reaction mixture. After the addtion, the reaction mixture was stirred for additional 1 hour to react.

After the reaction was completed, the reaction mixture was cooled to 60° C. and then sulfuric acid in the mixture was removed by adding with 100 ml of water, washing with water for 15 minutes with agitation and separating a water layer.

The resulting organic layer was analyzed by high speed liquid chromatography and the yield of N-cyclohexylmaleimide based on N-cyclohexylmaleamic acid used in Reference example 1 as starting material was 86.3 mol%.

EXAMPLE 2

19.7 g (0.1 mol of N-cyclohexylmaleamic acid, 180 ml of benzene, 27.8 ml (0.3 mol) of n-butylalcohol and 1.0 ml of conc. sulfuric acid were added to a four-neck flask (500 ml) equipped with a thermometer, a condenser with a water separator (Dean-Stark trap), a dropping funnel and an agitator. The mixture was heated with stirring at 80° C. and an esterification reaction was conducted for 1 hour by removing water generated by the reaction from the flask. Then 60 ml of benzene was added to the flask from the dropping funnel and the excess amount of n-butylalcohol was removed from the flask by refluxing and removing 60 ml of the reaction solvent under a reduced pressure.

180 ml of toluene and 2.0 ml of conc. sulfuric acid were further added to the reaction mixture and reacted at 90° C. for 3 hours With stirring. After the reaction was completed, the reaction mixture was cooled to 6020 C. and then sulfuric acid in the mixture was removed by adding with 100 ml of water, washing with water for 15 minutes with agitation and separating a water layer.

The resulting organic layer was analyzed by high speed liquid chromatography and the yield of N-cyclohexylmaleimide based on N-cyclohexylmaleamic acid, the starting material was 76.4 mol%.

EXAMPLE 3

19.7 g (0.1 mol) of N-cyclohexylmaleamic acid, 360 ml of toluene, 27.8 ml (0.3 mol) of n-butylalcohol and 1.0 ml of conc. sulfuric acid were added to a four-neck flask (500 ml) equipped with a thermometer, a condenser with a water separator (Dean-Stark trap), a dropping funnel and an agitator. The mixture was heated with stirring under a reduced pressure to keep a reaction temperature at 80° C. and an esterification reaction was conducted for 1 hour by removing water generated by the reaction from the flask. Then 60 ml of toluene was added to the flask from the dropping funnel and the excess amount of n-butylalcohol was removed from the flask by refluxing and removing 60 ml of the reaction solvent under a reduced pressure.

2.0 ml of conc. sulfuric acid was added to the reaction mixture and reacted at 110° C. for 3 hours with stirring. After the reaction was completed, the reaction mixture was cooled to 60° C. and then sulfuric acid in the mixture was removed by adding with 100 ml of water, washing with water for 15 minutes with agitation and separating a water layer.

The resulting organic layer was analyzed by high speed liquid chromatography and the yield of N-cyclohexylmaleimide based on N-cyclohexylmaleamic acid, the starting material was 72.9 mol%.

EXAMPLE 4 TO 7

The procedures of Examples 2 and 3 were repeated excepting that iso-butylalcohol or n-proplyalcohol were used instead of n-butylalcohol. The yields (mol%) of N-cyclohexylmaleimide were estimated on the basis of N-cyclohexylmaleamic acid, the starting material and listed in Table 1.

TABLE 1

| Example | Alcohol | Procedures | Yield (mol %) |
|---|---|---|---|
| 4 | iso-butylalcohol | Example 2 | 70.0 |
| 5 | iso-butylalcohol | Example 3 | 70.4 |
| 6 | n-propylalcohol | Example 2 | 71.8 |
| 7 | n-propylalcohol | Example 3 | 70.0 |

EXAMPLE 8

The esterification procedures of Reference example 1 and the imidation procedures of Example 1 were repeated excepting that N-n-butylmaleamic acid was used in place of N-cyclohexylmaleamic acid in the esterification. The resulting organic layer was analyzed by high speed liquid chromatography and the yield of N-butylmaleimide based on N-butylmaleamic acid, the starting material was 85.9 mol%.

EXAMPLE 9

The esterification procedures of Reference example 1 were repeated until the esterification reaction was completed and then the solvent was removed by a rotary evaporator. Then 180 ml of toluene was added to the resulting mixture and the imidation reaction was carried out for 2 hours under reflux. The resulting organic layer was analyzed by high speed liquid chromatography and the yield of N-cyclohexylmaleimide based on N-cyclohexylmaleamic acid, the starting material was 87.1 mol%.

COMPARATIVE EXAMPLE 1

9.85 g (0.05 mol) of N-cyclohexylmaleamic acid, 180 ml of toluene, 6.1 ml (0.15 mol) of methanol and 1.5 ml (0.025 mol) of conc. sulfuric acid were added to a three-neck flask (300 ml) equipped with a thermometer, a condenser with a water separator Dean-Stark trap and an agitator. The mixture was heated with stirring under a reduced pressure to keep a reaction temperature at 110 and a reaction was conducted for 3 hours by removing water generated by the reaction from the flask.

After the reaction was completed, the reaction mixture was cooled to 60° C. and then sulfuric acid in the mixture was removed by adding with 50 ml of water, washing with water for 15 minutes with agitation and separating a water layer.

The resulting organic layer was analyzed by high speed liquid chromatography and the yield of N-cyclohexylmaleimide based on N-cyclohexylmaleamic acid used in Reference example 1 as starting material was 32.2 mol%.

COMPARATIVE EXAMPLES 2 TO 7

In accordance with the procedures of Comparative example 1, the reactions were conducted by using 0.05 mol of N-Cyclohexylmaleamic acid, 0.15 mol of alcohols and 0.025 mol of conc. sulfuric acid. The yields (mol%) of N-cyclohexylmaleimide based on N-cyclohexylmaleamic acid are listed in Table 2.

TABLE 2

| Comp. example | Alcohol | Yield (mol %) |
|---|---|---|
| 2 | ethanol | 49.2 |
| 3 | n-butylalcohol | 57.9 |
| 4 | iso-butylalcohol | 55.4 |
| 5 | n-hexylalcohol | 51.2 |

TABLE 2-continued

| Comp. example | Alcohol | Yield (mol %) |
|---|---|---|
| 6 | benzylalcohol | 29.6 |
| 7 | not used | 7.8 |

REFERENCE EXAMPLE 2

157.6 g (0.8 mol) of N-cyclohexylmaleamic acid, 720 ml of toluene, 221.2 ml (2.4 mol) of iso-butylalcohol and 4 ml of conc. sulfuric acid were added to a three-neck flask (2 liter) equipped with a thermometer, a condenser with a water separator (Dean-Stark trap) and an agitator. The mixture was heated with stirring under a reduced pressure to keep a reaction temperature at 50° C. and an esterification reaction was conducted for 15 min by removing water generated by the reaction from the flask. Then 300 ml of water was added to the flask and separate a water layer to remove sulfuric acid.

Toluene in the resulting organic layer was evaporated under a reduced pressure to obtain a reaction mixture as a white slurry. 300 ml of n-hexane and 50 ml of benzene were added to the slurry followed by agitation, and then white crystals were collected by filtration. The resulant filtrate was washed with water and an aqueous solution saturated with sodium hydrogencarbonate until the filtrate exhibited weak alkalinity. After separation, the organic layer was dried over anhydrous sodium sulfate for 1 hour. Anhydrous sodium sulfate was separated, and hexane and benzene were evaporated under a reduced pressure to obtain a transparent solution. This solution was allowed to stand for a while to obtain crystals. The analysis by high speed liquid chromatography shows that these crystals were N-cyclohexylmaleamic acid iso-butylester and their purity was 99.0% or more.

Thus obtained N-cyclohexylmaleamic acid iso-butylester was used in the following examples.

EXAMPLE 10

Figure 1:
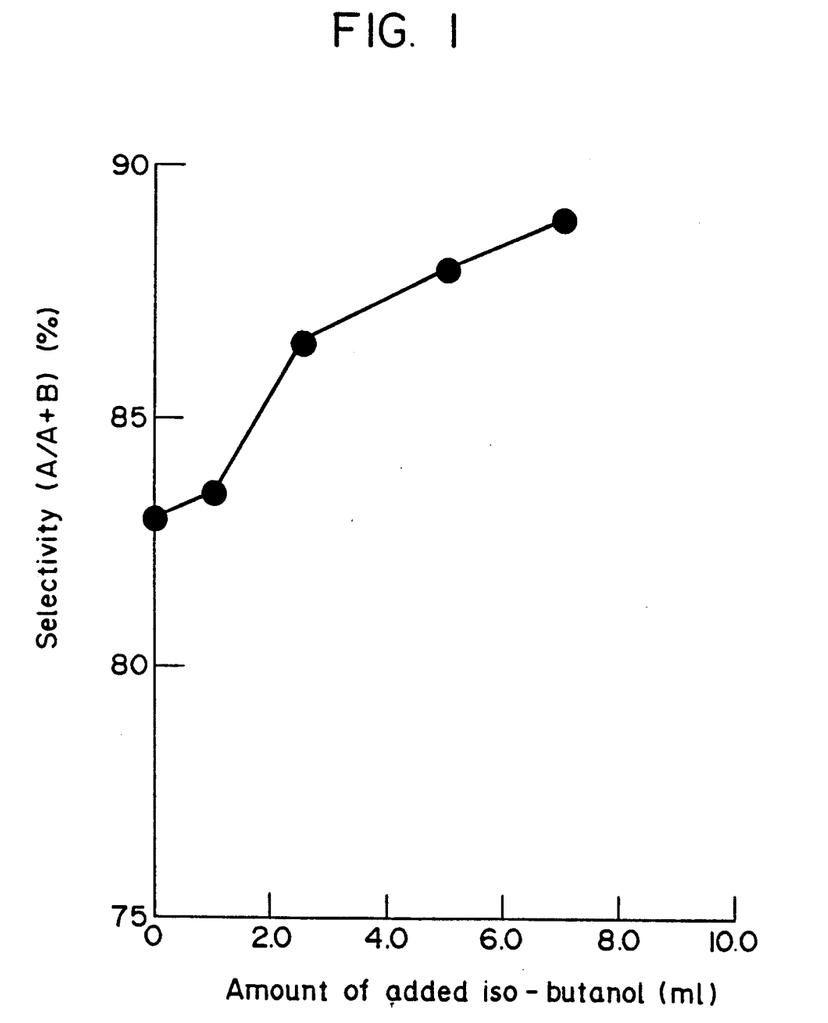
FIGS. 1 and 2 illustrate the effect of addition of alcohol on the selectivity of N-cyclohexylmaleimide.

12.7 g (0.05 mol) of N-cyclohexylmaleamic acid iso-butylester obtained in Reference example 2, 45 ml of toluene, 0.5 ml of conc. sulfuric acid and the prescribed amount (0, 1.6, 2.4, 4.8, 7.2 ml) of iso-butylalcohol were added to a three-neck flask (100 ml) equipped with a thermometer, a condenser with a water separator (Dean-Stark trap) and an agitator. The mixture was heated with stirring under reflux for 3 hours. After heating, the reaction mixture was cooled to 60° C. and sulfuric acid was removed by adding 50 ml of water, agitating for 15 min and separating a water layer.

The resulting organic layer was analyzed by high speed liquid chromatography. Yields (mol%) of produced N-cyclohexylmaleimide and maleamic acid di-iso-butylester based on N-cyclohexylmaleamic acid iso-butylester were obtained f rom the results and the selectivity of N-cyclohexylmaleimide was calculated in accordance with the formula below:

Selectivity (%) = $(A/A+B) \times 100$

A: yield of N-cyclohexylmaleimide
B: yield of maleamic acid diiso-butylester
The results are shown in FIG. 1.

EXAMPLE 11

Figure 2:
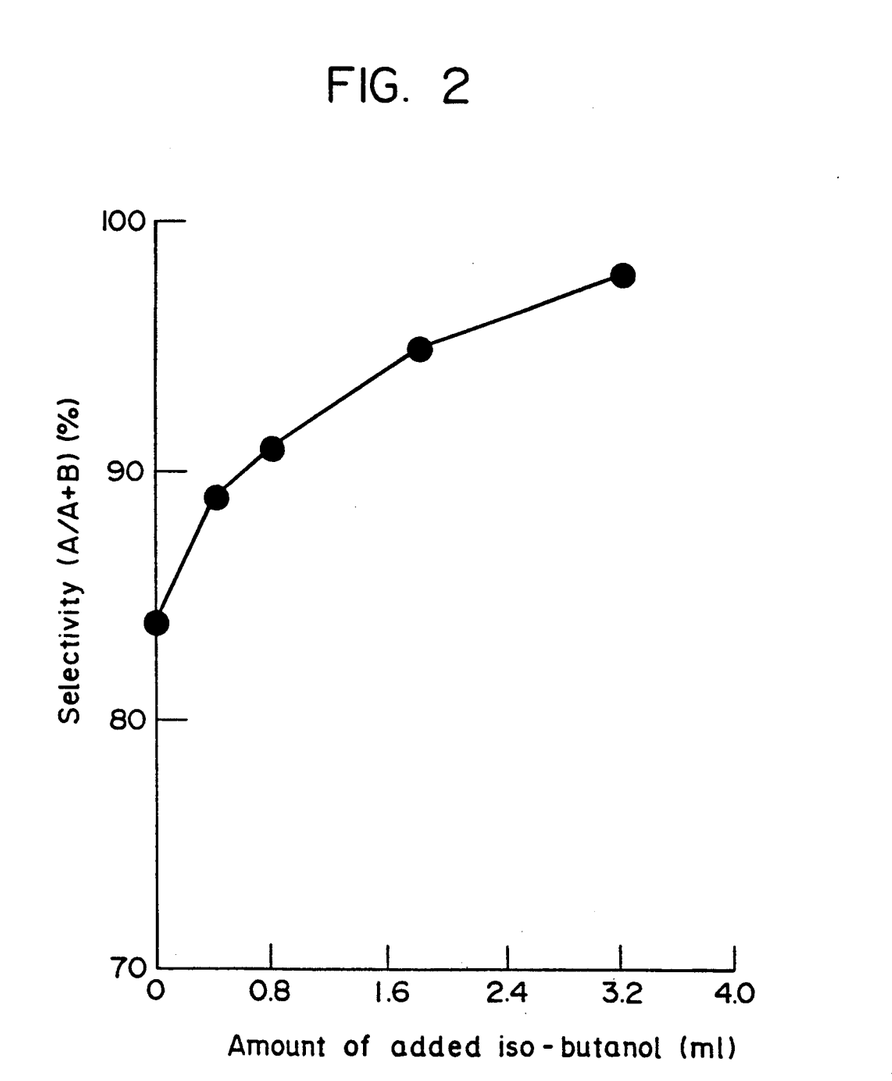

45 ml of toluene, 0.5 ml of conc. sulfuric acid and the prescribed amount (0, 0.6, 0.9, 1.7, 3.4 ml) of iso-butylalcohol were added to a three-neck flask (100 ml) equipped with a thermometer, a condenser with a water separator (Dean-Stark trap) and an agitator, and heated with stirring under reflux for 20 min. After heating, when the temperature of the mixture was dropped to 80° C., 12.7 g (0.05 mol) of N-cyclohexylmaleamic acid iso-butylester obtained in Reference example 2 was added to the flask and the resulting mixture was heated with stirring under reflux for 3 hours. After heating, the reaction mixture was cooled to 60° C. and sulfuric acid was removed by adding 50 ml of water, agitating for 15 min and separating a water layer.

The resulting organic layer was analyzed by high speed liquid chromatography. The selectivity of N-cyclohexylmaleimide was calculated in accordance with the same manner as that used in Example 10.

The results are shown in FIG. 2.

EXAMPLE 12

39.4 g (0.2 mol) of N-cyclohexylmaleamic acid, 180 ml of toluene, 55.3 ml (0.6 mol) of n-butylalcohol and 2.0 ml of conc. sulfuric acid were added to a four-neck flask (500 ml) equipped with a thermometer, a condenser with a water separator (Dean-Stark trap), a dropping funnel for supplying toluene and an agitator. The mixture was heated with stirring under a reduced pressure to keep a reaction temperature at 80° C. and an esterification reaction was conducted for 1 hour by removing water generated by the reaction from the flask. Then the pressure in the flask was returned to an atmospheric pressure and 0.1 g of p-methoxyphenol was added to the flask at 80° C. The flask was heated again at an atmospheric pressure and, from the time when toluene started to reflux, toluene was added to the flask at the rate of 180 ml/h and a reaction solvent was taken out from the water separator at the rate of 180 ml/h. The reaction was conducted with agitation by keeping this condition for 3 hours. After the reaction was completed, the reaction mixture was cooled to 60° C. and then sulfuric acid in the mixture was removed by adding with 100 ml of water, washing with water for 15 minutes with agitation and separating a water layer.

The resulting organic layer was analyzed by high speed liquid chromatography and the yield of N-cyclohexylmaleimide based on N-cyclohexylmaleamic acid, the starting material was 88.6 mol%.

The results are shown in Table 3.

COMPARATIVE EXAMPLE 8

The procedures of Example 12 were repeated excepting that p-methoxyphenol, a polymerization inhibitor, was not added and N-cyclohexylmaleimide was obtained. The results are shown in Table 3.

EXAMPLES 13 TO 19

The procedures of Example 12 were repeated excepting that polymerization inhibitors shown in Table 3 were used instead of p-methoxyphenol to obtain N-cyclohexylmaleimide.

The results are listed in Table 3.

TABLE 3

| Example | Polymerization inhibitor | Yield (%) |
|---|---|---|
| 12 | p-methoxyphenol | 88.6 |
| 13 | tert-butylcatechol | 91.0 |
| 14 | 2,4-dinitrophenol | 90.2 |
| 15 | hydroquinone | 91.3 |
| 16 | phenol | 87.7 |
| 17 | zinc di-n-butyl-di- | 83.4 |

TABLE 3-continued

| Example | Polymerization inhibitor | Yield (%) |
| --- | --- | --- |
|  | thiocarbamate |  |
| 18 | phenothiazine | 91.4 |
| 19 | dodecyl thiodipropionate | 83.4 |
| Comp. example 8 | not added | 66.0 |

EXAMPLE 20

17.1 g (0.1 mol) of N-tert-butylmaleamic acid, 90 ml of toluene, 27.9 ml (0.6 mol) of n-butylalcohol and 1.0 ml of conc. sulfuric acid were added to a four-neck flask (200 ml) equipped with a thermometer, a condenser with a water separator (Dean-Stark trap), a dropping funnel for supplying toluene and an agitator. The mixture was heated with stirring under a reduced pressure to keep a reaction temperature at 80° C. and an esterification reaction was conducted for 1 hour by removing water generated by the reaction from the flask, followed by removal of 50 ml of the reaction solvent. Then the pressure in the flask was returned to an atmospheric pressure and, 50 ml of toluene and 0.1 g of tert-butylcatechol were added to the flask at 80° C. The flask was heated again at an atmospheric pressure and, from the time when toluene started to reflux, toluene was added to the flask at the rate of 90 ml/h and the reaction solvent was taken out from the water separator at the rate of 90 ml/h. The reaction was conducted with agitation by keeping this condition for 4 hours. After the reaction was completed, the reaction mixture was cooled to 60° C. and then sulfuric acid in the mixture was removed by adding 50 ml of water, washing with water for 15 minutes with agitation and separating a water layer.

The resulting organic layer was analyzed by high speed liquid chromatography and the yield of N-tert-butylmaleimide based on N-tert-butylmaleamic acid, the starting material was 72.9 mol%.

COMPARATIVE EXAMPLE 9

17.1 g (0.1 mol) of N-tert-butylmaleamic acid, 90 ml of toluene, 27.9 ml (0.6 mol) of n-butylalcohol and 1.0 ml of conc. sulfuric acid were added to a three-neck flask (200 ml) equipped with a thermometer, a condenser with a water separator (Dean-Stark trap) and an agitator. The mixture was heated with stirring under a reduced pressure to keep a reaction temperature at 80° C. and an esterification reaction was conducted for 1 hour by removing water generated by the reaction from the flask, followed by removal of 50 ml of the reaction solvent under a reduced pressure. Then the Pressure in the flask was returned to an atmospheric pressure and 50 ml of toluene was added to the flask at 80° C. The flask was heated again at an atmospheric pressure with stirring under reflux of toluene for 4 hours to continue the reaction. After the reaction was completed, the reaction mixture was cooled to 60° C. and then sulfuric acid in the mixture was removed by adding 50 ml of water, washing with water for 15 minutes with agitation and separating a water layer.

The resulting organic layer was analyzed by high speed liquid chromatography and the yield of N-tert-butylmaleimide based on N-tert-butylmaleamic acid, the starting material was 55.6 mol%.

What we claim is:

1. A process for preparation of an N-substituted maleimide represented by formula (2):

from an N-substituted maleamic acid monoester represented by formula (1):

wherein $R^1$ represents an unsubstituted or substituted alkyl group having 1 to 20 carbon atoms, an unsubstituted or substituted cycloalkyl group having 3 to 12 carbon atoms, an unsubstituted or substituted naphthyl group; and $R^2$ represents an unsubstituted or substituted alkyl group having 1 to 7 carbon atoms, or an unsubstituted or substituted cycloalkyl group having 3 to 7 carbon atoms, wherein said N-substituted maleamic acid monoester is heated in the presence of an acid catalyst to eliminate an alcohol from the monoester.

2. A process of claim 1 wherein said N-substituted maleamic acid monoester is heated in the presence of the acid catalyst and an alcohol.

3. A process of claim 2 wherein a mixture of the acid catalyst and the alcohol is heated, the N-substituted maleamic acid monoester represented by formula (1) is added to the mixture and the resulting mixture is heated to eliminate an alcohol from the N-substituted maleamic acid monoester.

4. A process of claim 1 wherein said N-substituted maleamic acid monoester is heated in the presence of the acid catalyst and a polymerization inhibitor.

5. A process of claim 1 wherein said N-substituted maleamic acid monoester is heated in the presence of the acid catalyst, an alcohol and a polymerization inhibitor.

6. A process of claim 1 wherein said N-substituted maleamic acid monoester represented by formula (1) is produced by esterification of an N-substituted maleamic acid represented by formula (3):

wherein $R^1$ represents an unsubstituted or substituted alkyl group having 1 to 20 carbon atoms, an unsubstituted or substituted cycloalkyl group having 3 to 12 carbon atoms, an unsubstituted or substituted phenyl group, or an unsubstituted or substituted naphthyl group, in the presence of an acid catalyst and the alcohol represented by $R^2$—OH, wherein $R^2$ represents an unsubstituted or substituted alkyl group having 1 to 7 carbon atoms, or an unsubstituted or substituted cycloalkyl group having 3 to 7 carbon atoms.

7. A process for preparation of an N-substituted maleimide represented by formula (2):

comprising esterification of an N-substituted maleamic acid represented by formula (3):

in the presence of an acid catalyst and an alcohol represented by formula $R^2$—OH to obtain a reaction mixture containing an N-substituted maleamic acid monoester represented by formula (1):

and heating, in the presence of an acid catalyst, said reaction mixture at a temperature higher than that of esterification to eliminate the alcohol of formula $R^2OH$ from the N-substituted maleamic acid monoester represented by formula (1) and obtain the N-substituted maleimide represented by formula (2), wherein $R^1$ represents an unsubstituted or substituted alkyl group having 1 to 20 carbon atoms, an unsubstituted or substituted cycloalkyl group having 3 to 12 carbon atoms, an unsubstituted or substituted phenyl group, or an unsubstituted or substituted naphthyl group, and $R^2$ represents an unsubstituted or substituted alkyl group having 1 to 7 carbon atoms, or an unsubstituted or substituted cycloalkyl group having 3 to 7 carbon atoms, and wherein at least the heating of the reaction mixture containing the N-substituted maleamic acid monoester represented by formula (1) is conducted in the presence of a polymerization inhibitor.

8. A process of claim 1 or 7 wherein $R^1$ represents an unsubstituted or substituted alkyl group having 1 to 20 carbon atoms, or an unsubstituted or substituted cycloalkyl group having 3 to 12 carbon atoms.

9. A process of claim 8 wherein $R^1$ represents an unsubstituted or substituted alkyl group having 3 to 12 carbon atoms, or an unsubstituted or substituted cycloalkyl group having 5 to 10 carbon atoms.

10. A process of claim 1 or 7 wherein $R^2$ represents an unsubstituted or substituted alkyl group having 3 to 6 carbon atoms.

11. A process of claim 2 or 5 wherein the alcohol is at least one member selected from the group consisting of alcohols with an alkyl group having 1 to 7 carbon atoms and alcohols with a cycloalkyl group having 3 to 7 carbon atoms.

12. A process of claim 1 or 7 wherein the polymerization inhibitor is at least one member selected from the group consisting of alkylmonophenols, alkylbisphenols, thiodipropionic acid esters, dithiocarbaminic acid salts, salicylic acid salts, salicylic acid ester, phenothiazines, mercaptoimidazoles, trialkyl phosphites and copper salts.

13. A process of claim 1 wherein the heating temperature ranges from 80° to 170° C.

14. A process of claim 1 wherein the elimination of alcohol is carried out in a solvent.

15. A process of claim 1 or 7 wherein the acid catalyst is a Brnsted acid.

16. A process of claim 15 wherein the Brnsted acid is at least one sulfonic acid.

17. A process of claim 16 wherein the sulfonic acid is one member selected from the group consisting of sulfuric acid, anhydrous sulfuric acid, p-toluene sulfuric acid, methane sulfuric acid, benzene sulfuric acid, ethylsulfonic acid and octylsulfonic acid.

18. A process of claim 1 wherein the amount of acid catalyst ranges from 0.02 to 4 equivalents to the N-substituted maleamic acid monoester represented by formula (1).

19. A process of claim 7 wherein the esterification is conducted at a temperature from 30° to 110° C. and the elimination of alcohol is conducted at a temperature from 80° to 170° C.

* * * * *

UNITED STATES PATENT AND TRADEMARK OFFICE
CERTIFICATE OF CORRECTION

PATENT NO. : 5,087,705

DATED : February 11, 1992

INVENTOR(S) : Takashi Okada et al

It is certified that error appears in the above-identified patent and that said Letters Patent is hereby corrected as shown below:

Column 1, line 10, change "MMA" to --PMMA--.

Column 2, line 10, change "MMA" to --PMMA--.

Column 5, line 29, change "Brnsted" to --Brønsted" (both occurrences).

Column 16, line 34, change "Brnsted" to --Brønsted--.

Column 16, line 35, change "Brnsted" to --Brønsted--.

Signed and Sealed this

Twentieth Day of July, 1993

Attest:

MICHAEL K. KIRK

Attesting Officer

Acting Commissioner of Patents and Trademarks